United States Patent [19]

Ishida

[11] Patent Number: 4,916,384
[45] Date of Patent: Apr. 10, 1990

[54] APPARATUS FOR MEASURING THE SOOT PARTICLES CONTAINED IN THE EXHAUST GAS EMITTED FROM DIESEL ENGINES

[75] Inventor: Kozo Ishida, Kyoto, Japan
[73] Assignee: Horiba, Ltd., Kyoto, Japan
[21] Appl. No.: 940,162
[22] Filed: Dec. 9, 1986

Related U.S. Application Data

[63] Continuation of Ser. No. 601,843, Apr. 19, 1984, abandoned.

[30] Foreign Application Priority Data

Apr. 30, 1983 [JP]  Japan .................................. 58-76783

[51] Int. Cl.$^4$ ..................... G01N 27/62; G01N 15/00
[52] U.S. Cl. .................. 324/71.4; 324/464; 73/28
[58] Field of Search .............. 324/71.4, 454, 468, 324/464; 73/28, 23

[56] References Cited

U.S. PATENT DOCUMENTS

| | | | |
|---|---|---|---|
| 3,679,973 | 7/1972 | Smith, Jr. et al. | 324/71.4 |
| 4,361,028 | 11/1982 | Kamiya et al. | 73/28 |
| 4,531,402 | 7/1985 | Reif et al. | 324/464 X |
| 4,565,969 | 1/1986 | Olson et al. | 324/464 X |

FOREIGN PATENT DOCUMENTS 0826195  12/1959  United Kingdom ................ 324/464

Primary Examiner—Reinhard J. Eisenzopf
Assistant Examiner—Vinh P. Nguyen
Attorney, Agent, or Firm—Wenderoth, Lind & Ponack

[57] ABSTRACT

An apparatus and method for providing a continuous and precise measurement of the number of soot particles emitted in the exhaust gas of a diesel engine. A pair of electrodes is provided in the exhaust gas flow and a voltage is applied across the electrodes so as to develop an electrical current across the electrodes indicative of the conductivity, and therefore the quantity, of the soot particles in the exhaust gas. In accordance with one embodiment of the invention, the electrodes are located in a diluting conduit provided with a pump for providing a constant volume of diluted exhaust gas between the electrodes. In accordance with another embodiment of the invention, the electrodes are located in the exhaust pipe of the diesel engine.

12 Claims, 1 Drawing Sheet

APPARATUS FOR MEASURING THE SOOT PARTICLES CONTAINED IN THE EXHAUST GAS EMITTED FROM DIESEL ENGINES

This application is a continuation of now abandoned application Ser. No. 601,843, filed April 19, 1984.

BACKGROUND OF THE INVENTION

1. Field of the Invention

This invention relates to a measuring apparatus for continuously measuring fine particles, particularly the particles of soot contained in the exhaust gas emitted from diesel engines.

2. Description of the Prior Art

It is known that the fine particles in the exhaust gas of diesel engines are of two general types:
(1) White smoke or blue smoke which is a precursor of soot (an exhaust consisting of concentrated hydrocarbon drops and lubricating oil) which is called s.o.f. (soluble organic fraction) and which is soluble in an organic solvent, and
(2) Soot particles known as "dry soot", which is insoluble in an organic solvent.

Soot is not only unpleasant to see spewing out of the exhaust pipes of diesel vehicles, it is also unhealthy and dirty and is subject to U.S. environmental emission regulations. In the United States, the standard method of measuring soot concentrations in vehicle emissions recognized by the U.S. Environmental Protection Agency, which is responsible for promulgating and enforcing emission regulations, is based on the measurement of the weight of soot particles captured by a filter placed in the exhaust passage for a fixed period of time.

However, with this method of weighing the soot particles trapped by a filter, data cannot be collected on a continuous basis in the course of various trials during attempts to achieve improvements in the reduction of soot particles. In this regard, the makers of diesel vehicles have sought the development of a continuously measuring apparatus, by the operation of which it becomes feasible to determine on a real time basis the rate of emission of soot particles.

Prior devices for measuring the rate of emission of particulate matter continuously, such as devices which carry out the light scattering method and the optoacoustic method by a $CO_2$-laser, however, are sensitive not only to the soot particles, but also to the s.o.f. These devices therefore are not able to accurately measure the rate of emissions of soot particles only.

BRIEF SUMMARY OF THE INVENTION

The invention provides an apparatus and method for a continuous and precise measurement of the number of soot particles emitted in the exhaust gas of a diesel engine. A pair of electrodes is provided in the exhaust gas flow and a voltage is applied across the electrodes so as to develop an electrical current across the electrodes indicative of the conductivity, and therefore the quantity, of the soot particles in the exhaust gas. In accordance with one embodiment of the invention, the electrodes are located in a diluting conduit provided with a pump for providing a constant volume of diluted exhaust gas between the electrodes. In accordance with another embodiment of the invention, the electrodes are located in the exhaust pipe of the diesel engine.

BRIEF DESCRIPTION OF THE DRAWINGS

These and other aspects of the invention will be better understood from the following detailed description of the preferred embodiments of the invention, when taken with the accompanying drawings in which.

DETAILED DESCRIPTION OF THE PREFERRED EMBODIMENTS

Figure 1:
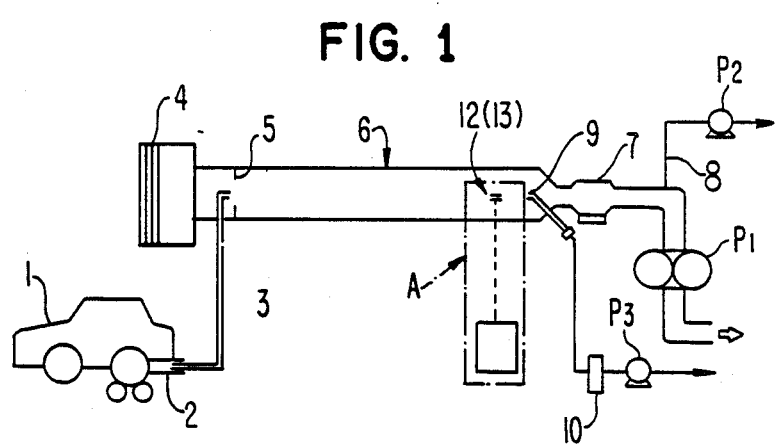
FIG. 1 is a partially sectional, partially schematic drawing of one embodiment of the apparatus is accordance with the invention.

Referring to FIG. 1, there is shown a system for analyzing a constant flow of diluted exhaust gas from a diesel engine, incorporating a measuring apparatus A for measuring the rate of emission of soot particles from the diesel engine on a continuous real time basis. The system includes a dilution tunnel 6 and an exhaust gas-introducing pipe 3 connecting the exhaust gas discharging pipe 2 of the diesel engine 1 to the dilution tunnel 6. Dilution tunnel 6 has both an air inlet provided with an air filter 4, for receiving the diluting air, and orifice walls 5 within tunnel 6 at the outlet of pipe 3 for creating turbulence, thereby causing mixing of the exhaust gas and diluting air as they flow through the orifice walls 5. A main pump $P_1$ is provided for maintaining a constant flow of the diluted exhaust gas through the tunnel 6; that is, to provide a constant flow rate of the sum of the exhaust gas from the introducing pipe 3 and the diluting air flow introduced through the filter 4. A heat exchanger 7 is provided in the dilution tunnel 6 for maintaining the temperature of the diluted exhaust gas at a constant level. A sample-gathering line 8 having a pump $P_2$ therein, is provided off the dilution tunnel 6 downstream of the heat exchanger 7 for providing a constant flow of diluted exhaust gas for use in a separate analysis of CO, HC, or $NO_x$.

Inserted in the dilution tunnel 6 downstream of the measuring apparatus A, but upstream of the heat exchanger 7, is a conventional probe 9 which draws with the use of a pump $P_3$ a flow of diluted exhaust gas at a velocity equal to the velocity of flow within the diluting tunnel 6. Such a conventional arrangement for drawing a flow exhaust gas from a main gas flow at a velocity equal to that of the main gas flow is disclosed in U.S. Pat. No. 3,699,814, particularly at column 7, lines 1–28 and FIG. 6. This diluted exhaust gas flow is directed through a filter 10 which filters the fine grains of soot contained in the exhaust gas so as to provide a means for measuring the accumulated quantity of soot particles as described in the above background of the invention. Thus, the overall system is capable of measuring the content of soot particles in the exhaust gas of a diesel engine on a real time basis, providing an analysis of other polutants such as CO, HC, or $NO_x$, and providing samples of the soot particles filtered from a constant volume of diluted exhaust gas.

Figure 2:
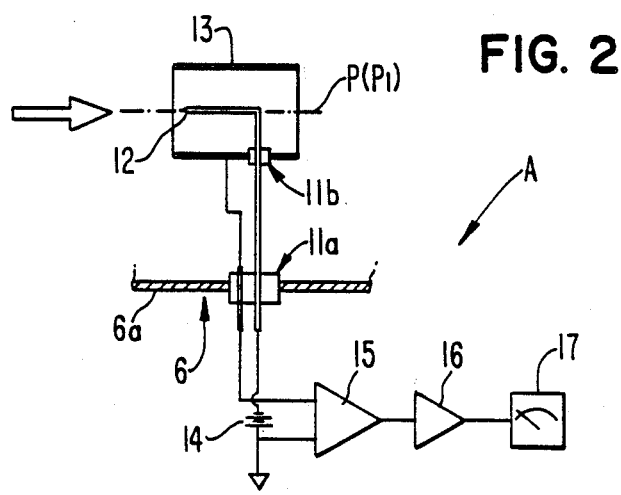
FIG. 2 is a partially sectional, partially schematic drawing of the detecting part thereof.

The apparatus A for measuring the quantity of soot particles is illustrated in FIG. 2. Referring to FIG. 2, the interior of the dilution channel 6 upstream of probe 9 is provided with a needle-shaped cathode electrode 12 supported on the tunnel wall 6a through an insulating body 11a with the axis of the electrode 12 lying parallel to the direction of diluted gas flow in the dilution tunnel 6. Surrounding the cathode electrode 12 is a cylindrical anode electrode 13 having its central axis P extending coaxially with the cathode electrode 12, the cathode electrode 12 having a radially extending portion extending through the wall of the anode electrode 13 through an insulating body 11b. Electrodes 12 and 13 are respectively electrically connected to a current amplifier 15 exterior of the wall 6a of the dilution tunnel 6. A DC voltage source 14 is provided across the electrodes 12 and 13. The output of the amplifier 15 is connected to a circuit 16 for linearizing the output of the amplifier 15, and a current indicator 17 is connected to the output of the circuit 16.

As is illustrated in FIGS. 1 and 2, the cylindrical anode electrode 13 is so sized and positioned as to be spaced a distance substantially greater than the radius thereof from the inner wall surface of the tunnel wall 6a, so that necessarily only a small proportion of the diluted exhaust gas will pass through the cylindrical anode electrode 13 and the remainder will flow between the electrode 13 and the tunnel wall 6a.

Figure 3:
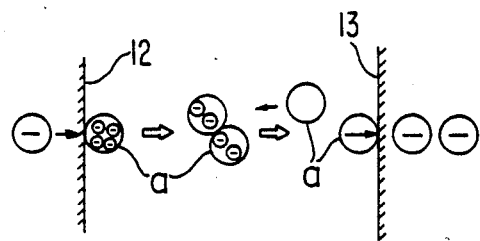
FIG. 3 is an explanatory diagram of the conducting process thereof.

The soot particles in the exhaust gas have a very high conductivity in comparison to the remaining contents of the exhaust gas, including the above mentioned s.o.f. For example, the conductivity of s.o.f. is less than $10^{-16}$ S/m, while the conductivity of the soot particles is approximately 30 S/m. When the exhaust gas containing soot particles passes between electrodes 12 and 13, a small current proportional to the quantity of soot particles contained in the exhaust gas flows between the electrodes 12 and 13. More precisely, the soot particles a become negatively charged when they strike the cathode electrode 12 and are then drawn toward the anode electrode 13. The number of said particles which reach anode electrode 13 is multiplied through electron diffusion as soot particles carrying multiple electron charges collide with other soot particles in the exhaust gas, as illustrated in FIG. 3.

Since any increase in the current between the electrodes 12 and 13 indicates a corresponding change in the conductivity of the exhaust gas in proportion to the quantity of soot particles therein, it is possible to continuously measure the quantity of soot particles passing between electrodes 12 and 13 on the basis of the conductivity as displayed on indicator 17. Furthermore, if the velocity of the diluted exhaust gas flow in tunnel 6 is kept constant, the conductivity displayed on indicator 17 also reflects the volumetric concentration of soot particles in the exhaust gas since the cross-sectional area of the cylindrically shaped electrode 13 is constant in the direction of gas flow, provided that the velocity of exhaust gas flow is taken into account.

In accordance with a modification of the present invention, if the velocity of exhaust gas flow in tunnel 6 varies continuously, a display of the quantity and concentration of soot particles in the exhaust gas can be obtained, for example, by providing an apparatus for detecting the velocity of the gas flow in tunnel 6 and applying the output of such apparatus, together with the output of the circuit 16, into a conventional general purpose computer which can easily be programmed to provide a reading of the soot particle concentration as a function of the measured conductivity and flow velocity of the diluted exhaust gas.

Figure 4:
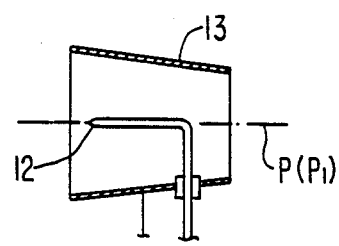
FIG. 4 is a sectional drawing of modified electrodes in the detecting part in accordance with another embodiment of the invention.

In accordance with another modification of the soot particle measuring apparatus in accordance with the present invention, the anode 13 may be frusto-conically shaped with the larger diameter opening located upstream of the lesser diameter opening thereof, as illustrated in FIG. 4.

In accordance with a still further modification of the present invention, the electrodes 12 and 13 may be arranged inside the exhaust pipe 2 or inside the exhaust gas introducing pipe 3. In accordance with this embodiment, the quantity and concentration of soot particles in the exhaust gas is measured directly without taking into account its dilution by diluting air in the diluting tunnel 6.

The invention is based on the fact that the conductivity of the soot particles in the exhaust gas is very much higher than that of the s.o.f. in that the changing conductivity of the soot particles in proportional to the change and its quantity in the exhaust gas. The present invention therefore makes it possible to measure the quantity or concentration of soot particles in a very accurate manner even at very low concentrations. The present invention is relatively simple in construction and inexpensive to manufacture. It can therefore be very helpful to manufacturers of diesel engines in estimating soot particle concentrations in the exhaust gas in the process of making improvements in the engine tending to reduce the amount of soot particles in the exhaust gas.

While particular embodiments of the present invention have been illustrated and described, it would be obvious to those skilled in the art that various changes and modifications can be made without departing from the spirit and scope of the invention. The appended claims are intended to cover all such modifications within the scope of the invention.

What is claimed is:

1. An apparatus for measuring the rate of emission of soot particles in the exhaust gas of a diesel engine, comprising a diluting conduit having an interior wall surface, means for injecting air and the exhaust gas into said diluting conduit so as to dilute the exhaust gas and flow within said interior wall surface, and means, disposed in the path of said exhaust gas and responsive to the conductivity of the soot particles in the exhaust gas, for producing an electrical current proportional to the quantity of soot particles in the exhaust gas, said producing means including a pair of spaced electrodes and means for applying a voltage thereacross, said pair of electrodes being disposed in said diluting conduit in spaced relation to said inner wall surface thereof, the cross-sectional area of a first space between said electrodes being a small proportion of the cross-sectional area of a second space between said interior wall surface and said electrodes whereby only a small proportion of the diluted exhaust gas passes between said electrodes and the remainder of the diluted exhaust gas passes through said second space between said electrodes and said interior wall surface.

2. An apparatus as in claim 1, wherein said inner wall surface is cylindrical and said electrodes comprise and elongated electrode extending parallel to the direction of flow of the diluted exhaust gas in said diluting conduit and a cylindrical electrode surrounding said elongated electrode in radially spaced relation thereto and substantially coaxial therewith and being open at opposite ends thereof inside said diluting conduit, said cylindrical electrode having a radius which is a small proportion of the radius of said interior wall surface.

3. An apparatus as in claim 1, wherein said electrodes include an elongated electrode extending parallel to the direction of flow of the diluted exhaust gas in said diluting conduit, and a frusto-conically shaped electrode surrounding and substantially coaxial with said elongated electrode, the larger diameter opening of said frusto-conically shaped electrode being upstream of the smaller diameter opening thereof with respect to the exhaust gas flow.

4. An apparatus as in claim 1, further comprising means for maintaining a constant flow of the diluted exhaust gas through said diluting conduit.

5. An apparatus as in claim 1, further comprising means for continuously measuring and providing a signal indicative of the rate of diluted exhaust gas flow through said diluting conduit, said apparatus further comprising means, responsive to said electrical current and said signal, for indicating the concentration of soot particles in the exhaust gas.

6. A method of measuring the rate of emission of soot particles in the exhaust gas of a diesel engine, comprising the steps of:
directing air and the exhaust gas from a diesel engine into a diluting conduit so as to obtain a flow of diluted exhaust gas in the diluting conduit;
disposing a pair of spaced electrodes having a cross sectional area substantially less than the interior cross sectional area of the diluting conduit in the diluting conduit such that a small proportion of the diluted exhaust gas passes between the electrodes and the remainder of the diluted exhaust gas passes between the electrodes and an interior wall surface of the diluting conduit;
applying a voltage across the electrodes;
measuring the electrical current produced between the electrodes; and
converting the magnitude of the measured electrical current to a value indicative of the number of soot particles in the exhaust gas.

7. A method as in claim 6, wherein said step of disposing comprises the step of disposing an elongated electrode parallel the direction of flow of the diluted exhaust gas in the diluting conduit and disposing a cylindrical electrode so as to surround the elongated electrode in radially spaced coaxial relation therewith such that the radial distance from the elongated electrode to the cylindrical electrode is a small proportion of the distance from the inner wall surface of the diluting conduit to the cylindrical electrode, and so that the small proportion of the diluted exhaust gas passes entirely through the cylindrical electrode without leaving the diluting conduit.

8. An apparatus as in claim 6, wherein said step of disposing includes the step of disposing an elongated electrode so as to extend parallel to the direction of flow of the diluted exhaust gas and disposing a frusto-conically shaped electrode substantially coaxial therewith, the larger diameter opening of the frusto-conically shaped electrode being upstream of one smaller diameter opening thereof with respect to the exhaust gas flow.

9. A method as in claim 6, further comprising the step of maintaining a constant flow of the diluted exhaust gas through the diluting conduit.

10. A method as in claim 6, further comprising the steps of continuously measuring and providing a signal indicative of the rate of diluted exhaust gas flow through the diluting conduit, and indicating, as a function of the electrical current and the signal, the concentration of soot particles in the exhaust gas.

11. An apparatus for measuring the rate of emission of soot particles in the exhaust gas of a diesel engine, comprising: a diluting conduit having an inner wall surface; means for injecting air and exhaust gas into said diluting conduit so as to dilute the exhaust gas whereby a diluted exhaust gas flows through the inner wall surface of said diluting conduit; means for maintaining a constant flow of the diluted exhaust gas through said diluting conduit; and means, disposed in the path of the diluted exhaust gas and responsive to conductivity of the soot particles in the diluted exhaust gas, for producing an electrical current proportional to the quantity of soot particles in the exhaust gas, said producing means including a pair of spaced electrodes and means for applying a voltage thereacross, said pair of electrodes being disposed in said diluting conduit, said electrodes comprising an elongated electrode extending parallel to the direction of flow of the diluted exhaust gas in said diluting conduit and an outer electrode circular in cross section surrounding said elongate electrode in radially spaced relation thereto and substantially coaxial therewith, the radius of said outer electrode being a small proportion of the radial distance between said outer electrode and said inner wall surface of said diluting conduit, whereby a small proportion of the diluted exhaust gas passes entirely through said outer electrode without leaving said diluting conduit, the remainder of the diluted exhaust gas passing through a space between said outer electrode and the inner wall surface of said diluting conduit.

12. A method of measuring the rate of emission of soot particles in the exhaust gas of a diesel engine, comprising the steps of:
directing air and the exhaust gas from a diesel engine into a diluting conduit having an inner wall surface so as to obtain a constant flow of diluted exhaust gas within the inner wall surface of the diluting conduit;
disposing an elongated electrode in the diluting conduit so as to be disposed in the flow of diluted exhaust gas and so as to extend parallel to the direction of flow of the diluted exhaust gas;
disposing an outer electrode circular in cross section in the diluting conduit so as to surround the elongated electrode in radially spaced coaxial relation thereto such that a small proportion of the diluted exhaust gas passes between the elongated electrode and the outer electrode without leaving the diluting conduit;
applying a voltage across the elongated and outer electrodes;
measuring the electrical current produced between the elongated and outer electrodes; and
converting the magnitude of the measured electrical current to a value indicative of the number of soot particles in the exhaust gas.

* * * * *